United States Patent [19]

Demer

[11] Patent Number: 4,781,192
[45] Date of Patent: * Nov. 1, 1988

[54] BALLOON DILATION APPARATUS

[75] Inventor: Linda L. Demer, Houston, Tex.

[73] Assignee: Baylor College of Medicine, Houston, Tex.

[*] Notice: The portion of the term of this patent subsequent to Mar. 24, 2004 has been disclaimed.

[21] Appl. No.: 944,772

[22] Filed: Dec. 22, 1986

[51] Int. Cl.$^4$ ............................................. A61M 29/02
[52] U.S. Cl. ...................................... 128/344; 604/97
[58] Field of Search .............. 128/344, DIG. 12, 782; 604/97, 98, 100, 52, 53; 33/125 R

[56] References Cited

U.S. PATENT DOCUMENTS

| | | | |
|---|---|---|---|
| 3,336,925 | 8/1967 | Thompson, III | 604/155 |
| 3,420,222 | 1/1969 | Noe et al. | 128/782 |
| 3,456,649 | 7/1969 | Jewett | 604/155 |
| 3,782,188 | 1/1974 | Korber et al. | 128/782 |
| 4,651,738 | 3/1987 | Demer et al. | 128/344 |

Primary Examiner—C. Fred Rosenbaum
Assistant Examiner—Frank Wilkens
Attorney, Agent, or Firm—Fulbright & Jaworski

[57] ABSTRACT

Disclosed is an improved and simplified apparatus for simultaneously monitoring the pressure and volume of liquid in the balloon catheter as the balloon is being dilated, such as in performing angioplasty procedures and other parts of the body susceptible to balloon dilation, such as dilation of the esophagus, the uretha, and the like.

3 Claims, 2 Drawing Sheets

BALLOON DILATION APPARATUS

FIELD OF THE INVENTION

The present invention is in the field of balloon dilation apparatus useful in arterial dilation of coronaries and peripheral arteries and other parts of the body subject to balloon dilation, such as the esophagus and uretha, which may have narrowing due to scarring or fibromuscular hyperplasia.

BACKGROUND OF THE INVENTION

Arteriosclerosis is a genera term which refers to any of a group of diseases in which the lumen of an artery becomes narrowed or blocked. The most common and important form of arteriosclerosis, especially in Western societies, is the disease known as atherosclerosis. In atherosclerosis, there is an accumulation of lipids in the intimal, or inner, layer of the affected artery. The resulting intimal thickening restricts the flow of blood so as to hinder the functioning of, or permanently damage, the organ which the artery feeds. These accumulations of lipids tend to be localized and can occur in coronary, cerebral, or peripheral arteries. They will hereinafter be referred to synonymously as lesions, plaques, or atheromas.

The lipid accumulation is made up of free lipid and smooth muscle cells which have proliferated and taken up lipid. As the disease progresses, the lesion may begin to absorb calcium which causes it to harden and may also be composed of blood which has clotted in response to the presence of the atheroma. Although the process of plaque formation is not completely understood, it is known to be progressive, and atherosclerotic plaques may vary greatly in their physical characteristics.

Another cause of arterial narrowing, especially in patients with acute myocardial infarction (heart attack), is formation or embolization of a thrombus (clot) within a coronary artery.

Treatment of atherosclerosis and occlusive thrombi is aimed at alleviating the diminished blood flow. This can sometimes be done by medical means which cause the smooth muscles of the arterial walls to relax and thereby dilate the artery. Other treatment methods are directed toward physiological compensation for the reduced blood flow. In cases where the artery is severely occluded, however, there is no reasonable alternative but to try to re-establish a lumen of proper diameter. A number of surgical procedures have been developed toward this end. These include endarterectomy, in which the plaque or thrombus is surgically removed, and by-pass grafts, in which a segment of artery or vein from elsewhere in the body is removed and reattached in place of the occluded artery. These procedures are major surgical operations and present a number of disadvantages to a patient including financial cost, inconvenience, and the risk of complications associated with any major surgery. Therefore, in the past several years, methods of re-establishing the patency of an occluded artery have been developed which are relatively noninvasive and present less risk to a patient than conventional surgery. One such method is transluminal angioplasty.

Other parts of the body are subject to balloon dilation, such as the esophagus and uretha, which may have narrowing due to scarring or fibromuscular hyperplasia, which is abnormal inward growth of the normal living tissue of an artery or other vessel.

DESCRIPTION OF THE PRIOR ART

The conventional method of performing transluminal angioplasty uses a special double lumen catheter. The first or inner lumen allows passage of a guide wire. Concentric with this lumen is a second lumen which connects to a sausage-shaped segment or balloon at the distal end of the catheter. The second lumen and balloon are generally filled with diluted contrast media. Contrast media is radio-opaque liquid which makes visualization of the catheter possible by means of X-rays. The procedure first involves selecting a convenient place to introduce the catheter into the arterial system of the patient, such as the femoral artery of the leg. Next, the catheter is guided to the blocked artery. This is done manually and with the aid of an X-ray monitor. When the catheter is appropriately positioned, the guide wire is advanced to and past the point of obstruction. The balloon catheter, which surrounds the guide wire, is then advanced along with the guide wire until it is surrounded by the occluding plaque. The balloon, made of material with high tensile strength and low elasticity, is inflated to a pressure as high as 15 atmospheres. As the balloon expands, it creates a larger inner diameter within the occluded artery. It is not known with certainty what physical processes occur within the occluded artery in response to the balloon inflation, but the usual method is to inflate the balloon to a certain predetermined pressure and repeat the inflation an arbitrary number of times. The balloon is then collapsed and retracted. The site of the obstruction is then examined angiographically; and, if the artery is still occluded, a decision is made either to repeat the angioplasty procedure or to resort to some other option.

As aforementioned, the procedure involves inflating the balloon to a predetermined pressure. Although the operator may attempt to observe the size of the balloon during the inflation by means of the X-ray monitor, unless the pressure is measured, the bursting pressure of the balloon may be exceeded causing rupture. Therefore, practitioners have realized the need for continuous monitoring of the fluid pressure within the balloon. As it is conventional to inject fluid into the balloon with a syringe, the most obvious method is to interpose a T-fitting between the delivery end of the syringe and the balloon catheter. A standard pressure transducer can then be connected to the T-fitting and the fluid pressure within measured. U.S. Pat. No. 4,370,982 discloses a method for measuring fluid pressure without the transmitter coming in contact with the working medium. The '982 patent also discloses an injection device which uses a threaded member which when rotated produces translational motion of the syringe plunger. The relatively slow inflation is supposed to reduce further the risk of balloon rupture.

Another relevant patent is U.S. Pat. No. 4,446,867 which discloses a method and apparatus for generating pulses of pressure within the balloon catheter. As set above, some atheromas become hard due to calcification and therefore resist dilation by the balloon. The '867 patent represents an attempt to deal with this problem by inflating the balloon so rapidly that the plaque is broken. Although the specification of the '867 patent recites that pieces of broken plaque will be removed by normal cardiovascular processes, it seems obvious that such fragments may flow downstream and become lodged in a smaller artery, thereby completely blocking blood flow. As pieces of plaque may break off during conventional angioplasty procedures even without using the pulsed pressure method of the '867 patent, it is important to know when this has occurred so that remedial steps may be taken.

Prior to the method and apparatus disclosed in U.S. application Ser. No. 726,081, filed Aug. 2, 1985, one major problem with transluminal angioplasty was that theretofore there has been no means of evaluating the efficacy of the procedure contemporaneous with the performing of it. This has resulted in the establishment of arbitrary performance protocols whereby the balloon is inflated repeatedly an arbitrary number of times. Because the pressures involved are necessarily high, each subsequent inflation presents a risk of balloon rupture. It would be advantageous if the operator had some means of judging when the procedure had succeeded or failed and whether a subsequent inflation could be expected to succeed. As coronary lesions vary greatly in their physical characteristics, what is needed is a means of monitoring the underlying physical events occurring within the occluded artery as the balloon is inflated. Not only would this be helpful during the performance of the procedure itself, but it would make possible a more accurate prognosis of the course of the patient's disease and aid in evaluating other treatment options.

The method and device disclosed in U.S. application Ser. No. 762,081 filed Aug. 2, 1985 accomplishes this objective by providing for the simultaneous monitoring of both pressure and volume changes occurring within the balloon as the angioplasty procedure is performed. By the use of basic physical principles, the pressure-volume curves thus generated can be correlated with the physical changes taking place within the occluded artery. In this device a linear potentiometer is attached in parallel with an inflation syringe which monitors the position of the plunger and thus syringe volume. This is a relatively complex design, and it would be highly advantageous to provide a simpler and more manageable design to accomplish the foregoing objectives.

SUMMARY OF THE INVENTION

The present invention is directed to a simple and easily manageable apparatus which accomplishes simultaneous monitoring of both pressure and volume changes occurring within the balloon as it is dilated, such as during the performance of the angioplasty and other dilation procedures.

The apparatus comprises a syringe having a cylinder and a piston moveably mounted in the cylinder effective to fill a balloon catheter with liquid, a pressure transducer operable to measure pressure of liquid in the balloon catheter, a linear variable differential transformer (LVDT) including a hollow transformer, a core, preferably a small metal cylinder moveable in the hollow transformer, the syringe and LVDT being connected together in an end-to-end or axial direction, and a non-ferrous shaft moveably extending through the LVDT and into the syringe cylinder connected to the piston, the shaft carrying the core, so that axial or longitudinal movement of the shaft moves the piston and core simultaneously thereby generating a signal proportional to the core's axial position within the transformer and thereby the position of the piston in the syringe cylinder, and amount of liquid displaced from the syringe into the balloon catheter, and includes a readout monitor which simultaneously monitors pressure and volume changes occurring within the balloon.

As previously mentioned, the apparatus is not only useful in arterial dilation of coronaries and peripherial arterials, but also for other parts of the body subjected to balloon dilation, such as the esophagus and uretha, which may have narrowing due to scarring or fibromuscular hyperplasia, which is abnormal inward growth of the normal living tissue of an artery or other vessel.

Advantageously, the apparatus can utilize components readily available on the market, and it is a relatively simple and easily managed apparatus.

Accordingly, it is an object of the invention to provide a relatively simple and easily managed apparatus to fill a balloon catheter with liquid and which monitors both pressure and volume changes occurring within the balloon catheter as the balloon is dilated, sush as in performing the angioplasty and other dilation procedures.

It is a further object of the present invention to provide a syringe, a pressure transducer, a linear variable differential transformer (LVDT), the syringe and LVDT combined together with a common axis so that axial movement of a single rod carrying the syringe plunger and the core of the LVDT displaces liquid from the syringe into the balloon catheter and indicates the volume thereof by the position of the core in the LVDT, and a readout monitor for the volume and pressure, thereby providing simultaneous monitoring of both pressure and volume occurring within the balloon as it is dilated.

Other and further objects and advantages of the invention appear throughout the specification and claims.

DESCRIPTION OF THE INVENTION

Figure 4:
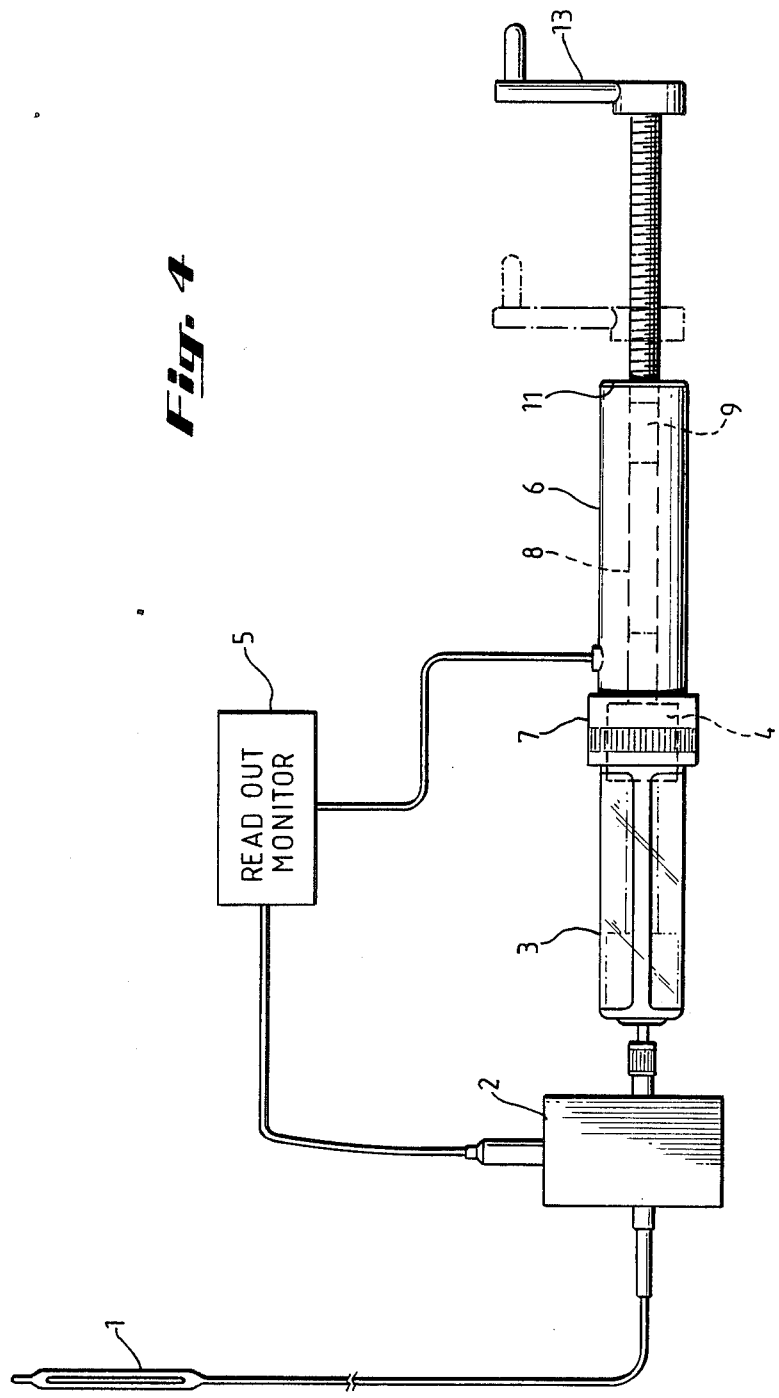
FIG. 4 is a drawing of the device used to perform the angioplasty procedure in accordance with the present invention.

The best mode and preferred embodiment of the invention is illustrated in FIG. 4. The proximal end of the balloon catheter 1 is attached to the inflation syringe 3. The syringe is of standard type but modified for reasons which will be apparent below. A plunger or piston 4 moves through the barrel or cylinder of the syringe 3 displacing liquid, such as diluted contrast media, into the balloon catheter 1.

Interposed between the balloon catheter 1 and the inflation syringe 3 is an electronic pressure transducer 2 of conventional type. An electronic signal proportional to the fluid pressure existing within the catheter is then fed to a readout monitor 5, such as an oscilloscope, liquid crystal display, plotter, and the like for real-time display. Any type of electronic recording device can be used.

A conventional linear variable differential transformer (LVDT) 6 is secured to the syringe base 7 such as by threading or other suitable means. The LVDT is of conventional design and has an axial passage through which the shaft 8 moves. The shaft 8 extends into the syringe 3 and is connected to the plunger or piston 4. A magnetic core 9 is secured in the shaft 8, such as by threading or other suitable means, the core 9 being disposed in the shaft 8 so it moves axially in passage of the LVDT 6.

Thus, axial or longitudinal movement of the shaft 8 moves the plunger or piston 4 and the core 9 the same axial or longitudinal distance; and the travel of the core 9 along the inside of the LVDT 6 generates a signal proportional to the core's axial position within the LVDT 6. In this way, the signal produced by the LVDT 6 is proportional to the volume of fluid displaced from the syringe 3, which represents the volume of the fluid contained by the balloon at any given time. By displaying the pressure and volume inputs simultaneously, a curve is generated in the read-out monitor 5 wherein one axis corresponds to pressure and the other axis corresponds to volume, when the read-out monitor is an oscilloscope. The information contained in this curve enables one to draw certain conclusions regarding the physical process taking place during the dilation process which is subsequently explained.

The shaft 8 is finely threaded generally along its length so that, when the shaft is turned, the shaft moves longitudinally or axially through an oppositely threaded member 11 preferably attached to the LVDT, although it may be otherwise attached. In this way, slow and even displacement of liquid into the balloon catheter is produced by rotating the shaft 8. The more fine the threads, of course, the slower will be the fluid displacement. A hand crank 13 is secured to the shaft 8 to facilitate the balloon inflation process. Preferably, the threads should be fine enough to provide an even and slow movement of the shaft 8 to prevent the production of transient pressure waves in liquid displaced by the piston 4 in the syringe 3 into the balloon catheter 1.

In operation, rotation of the handle 13 rotates the shaft 8 causing axial or longitudinal movement of the shaft 8, and hence simultaneous axial movement of the core 9 in the LVDT 6 and the plunger or piston 4 in the syringe 3 thereby displacing liquid into the balloon catheter 1. As this occurs, the fluid pressure and the displacement of liquid as indicated by the axial position of the core 16 are indicated on the read-out monitor 5. Thus, simultaneous monitoring of both pressure and volume occurring within the balloon catheter is provided as the angioplasty procedure is performed.

Figure 1:
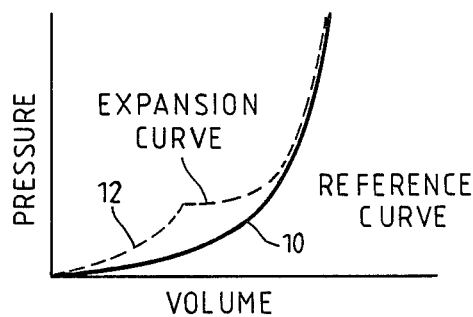
FIG. 1 depicts the pattern of a typical pressure-volume curve generated when an expanding balloon compacts or compresses or remolds the plaque material against the artery wall.
Figure 2:
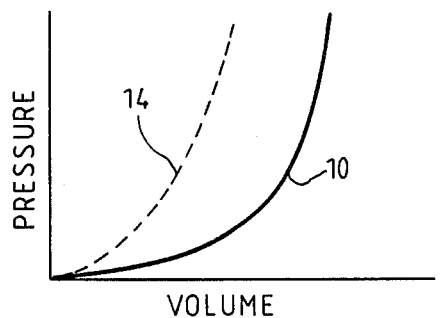
FIG. 2 depicts the pattern of a typical pressure-volume curve generated when an expanding balloon stretches the artery wall itself.
Figure 3:
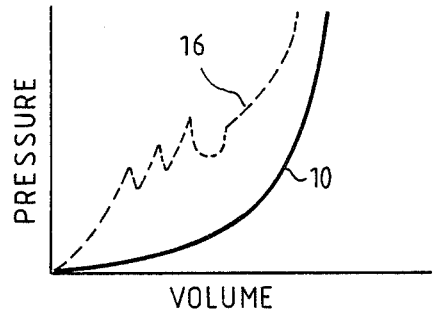
FIG. 3 depicts the pattern of a typical pressure-volume curve generated when an expanding balloon causes fractures in a plaque or tears in vessel lining.

FIGS. 1-3 represent volumes and pressures within the balloon catheter 10 by using the apparatus of FIG. 4. More specifically, FIGS. 1-3 depict expansion curves generated by dilating models of arterial lesions with three different types of behavior. Superimposed on all three figures is the expansion curve 10 of the balloon expanded by itself. This represents the compliance of the balloon alone and will be used as the reference curve.

Referring first to FIG. 1, expansion curve 12 shows that, as the pressure is raised initially, there is little change in the volume of the balloon as compared with the reference curve 10. This indicates that the atherosclerotic plaque which surrounds the balloon is preventing the balloon from expanding. As the pressure is increased further, however, the pressure within the balloon becomes great enough to overcome the resistance of the plaque material. At this point the occluded artery begins to dilate as the balloon expands. It is not clear whether the plaque material is actually compressed so as to occupy less volume or is deformed so as to be redistributed along the length of the artery, but what is important is that the expansion takes place at relatively constant pressure. At any given point along the curve, the pressure of the fluid within the balloon is exactly balanced by the pressure exerted by the surrounding plaque. A region of constant pressure, or isobaric, expansion indicates that the plaque material is exerting the same force irrespective of the extent of the plaque's deformation. The theory of the properties of materials would predict that the stress exerted on the plaque had exceeded the yield point of the plaque material This would mean that the plaque material is being deformed plastically rather than elastically. This is consistent with a young or at least still malleable atheroma which can be expected to retain the deformation produced by the expanded balloon. Thus, when an expansion curve like that of FIG. 1 is obtained, the operator may infer that the angioplasty procedure has been relatively successful and no further inflation cycles are necessary, especially if a repeat inflation yields a curve superimposed on curve 10. Furthermore, the knowledge that the atheroma responded to the procedure in this way is useful in the subsequent management of the patient's atherosclerotic disease.

These concepts make it easier for the cardiologist when observing incomplete balloon expansion versus complete balloon expansion. Joining of the curves means full dilation of the lesion, and superimposition at low pressures indicates complete dilation of the lesion at low pressure. The operator wants to see the curves join at low pressure.

Next, in FIG. 2, is an expansion curve 14 which indicates that, as the balloon expands against the occluded artery, the artery exerts increasing force against the balloon. This would lead one to conclude that the lesion is acting like a spring and storing the work of expansion only to return to its former occluded shape when the balloon is deflated. This behavior may indicate an unyielding lesion. This has been found experimentally to be the case although with repeated inflations the curve sometimes moves closer to the reference curve indicating that the artery is becoming more compliant. Unlike the case in FIG. 1, the balloon has not been fully expanded, the lesion persists in infringing on the balloon, as in an extremely rigid, perhaps calcified lesion. In any case, an expansion curve like that in FIG. 2 indicates a less desirable result for the patient than that in the first example above. What happens on the second inflation of the balloon really indicates whether the lesion is soft but bouncing back, like a clot. If the curve does not shift closer to the reference, then the lesion is just bouncing back, even if the curves join at higher pressures.

Finally, FIG. 3 shows an expansion curve 16 exhibiting sharp drops in pressure as the balloon expands. A sudden decrease in the pressure exerted against the balloon by the occluded artery can only mean that a stress relieving fracture of some kind has occurred. One can then infer that either the plaque fractured or that there was an abrupt tear in the inner lining of the artery and that remedial steps may need to be taken to prevent dissection, the process in which blood flow leaks into the crack (either of the plaque or innerlining) and forces the downstream portion into the artery, occluding flow and causing infarction or need for emergency surgery. One such remedial step might be to inflate the balloon a second time, although at a lower pressure, in order to "tack" the plaque fragments down and prevent dissection. Anticoagulant therapy may also be indicated since such a fracture contributes to formation of clots.

In generating the expansion curves discussed above, the particular instrumentation used must be able to respond to the extremely small changes in volume involved when the balloon expands as well as pressures reaching 15 atmospheres. The inflation syringe described in the preferred embodiment was also constructed with a shaft possession screw-type thread fine enough so that many rotations are necessary to move the shaft through the oppositely threaded annular member. A slow and even displacement of fluid into the balloon is necessary to avoid introducing artifacts into the pressure signal and obscuring the information contained therein. That is, a properly constructed expansion curve only contains pressure values which have been obtained after any transient pressure waves in the fluid have died out. The present invention provides a simple and an easily and readily manageable device or instrument for transluminal angioplasty in which both pressure and volume changes occurring within the balloon are monitored as the angioplasty procedure is performed.

In other balloon dilations, such as dilation of the esophagus and uretha, the same procedure is used, and a read out of both volume and pressure is obtained thereby providing complete monitoring of the particular procedure being performed.

Accordingly, the present invention is well suited and adapted to attain the ends and carry out the objects and has the advantages and features set forth as well as others inherent therein. While a presently preferred embodiment and uses of the invention have been given for the purpose of disclosure, changes therein, modifications thereto, and other uses thereof can be made which are within the spirit and scope of the invention as defined by the following claims.

What is claimed is:

1. An apparatus for performing balloon dilation and indicating the pressure and volume of the balloon during dilation comprising:
   a syringe for filling a balloon catheter with liquid,
   the syringe including a cylinder and a piston moveable axially in the cylinder effective to displace liquid in the syringe,
   liquid passage means adjacent an end of the cylinder for passage of the displaced liquid to the balloon catheter,
   a linear variable differential transformer having an axial bore and a core moveable axially in the bore effective to generate an electrical signal proportional to the core's axial position in the transformer,
   the syringe and the linear variable differential transformer being disposed together in end to end relationship,
   a shaft moveable axially within the syringe cylinder and the axial bore of the transformer, one end connected to the piston in the syringe cylinder, and the shaft in the bore of the transformer being nonferrous and carrying the core,
   whereby movement of the shaft causes simultaneous axial movement of the piston and the core and produces the electrical signal proportional to the core's axial position in the transformer and thereby the volume of the liquid displaced from the syringe cylinder into the balloon catheter,
   a pressure transducer in fluid communication with liquid in the liquid passage effective to produce an electrical signal proportional to the liquid pressure, and
   means for displaying the electrical signals produced by the linear variable differential transformer and the pressure transducer thereby displaying present and past values of the liquid pressure and volume existing within said balloon catheter.

2. The apparatus of claim 1 where,
   the shaft is threaded and includes a threaded bore hole means through which the shaft threadedly extends whereby the threaded shaft moves axially through the bore hole means when the shaft is rotated.

3. The apapratus of claim 2 where,
   threads of the threaded shaft and bore hole are constructed so finely that no transient pressure waves are produced within the liquid.

* * * * *